(12) United States Patent
Truncale et al.

(10) Patent No.: US 7,723,108 B2
(45) Date of Patent: May 25, 2010

(54) SOFT TISSUE PROCESSING

(75) Inventors: Katherine Gomes Truncale, Hillsborough, NJ (US); Jeffrey Stuart Cartmell, Freehold, NJ (US); Carina Syring, Basel (CH); Rudiger Von Versen, Basdorf (DE); Manh-Dan Ngo, Rochester, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 10 days.

(21) Appl. No.: 11/375,026

(22) Filed: Mar. 15, 2006

(65) Prior Publication Data
US 2006/0275377 A1 Dec. 7, 2006

Related U.S. Application Data

(60) Provisional application No. 60/662,078, filed on Mar. 16, 2005.

(51) Int. Cl.
*C12N 5/00* (2006.01)
(52) U.S. Cl. ............... 435/378; 435/381; 623/23.72
(58) Field of Classification Search ................ 435/378, 435/381; 623/23.72
See application file for complete search history.

(56) References Cited

U.S. PATENT DOCUMENTS

| 4,776,853 | A | | 10/1988 | Klement et al. | |
|---|---|---|---|---|---|
| 5,336,616 | A | | 8/1994 | Livesey et al. | |
| 5,364,756 | A | | 11/1994 | Livesey et al. | |
| 5,460,962 | A | | 10/1995 | Kemp | |
| 5,780,295 | A | | 7/1998 | Livesey et al. | |
| 5,997,575 | A | * | 12/1999 | Whitson et al. | 623/1.1 |
| 6,194,136 | B1 | | 2/2001 | Livesey et al. | |
| 6,682,695 | B2 | | 1/2004 | MacPhee et al. | |
| 6,734,018 | B2 | | 5/2004 | Wolfinbarger, Jr. et al. | |
| 7,087,089 | B2 | | 8/2006 | Patel et al. | |
| 7,121,999 | B2 | | 10/2006 | Abraham et al. | |
| 7,175,841 | B2 | * | 2/2007 | Badylak et al. | 424/93.7 |
| 2001/0000804 | A1 | * | 5/2001 | Goldstein et al. | 623/23.72 |
| 2003/0035843 | A1 | | 2/2003 | Livesey et al. | |
| 2004/0180042 | A1 | | 9/2004 | Cook et al. | |
| 2005/0013836 | A1 | * | 1/2005 | Raad | 424/400 |
| 2005/0013872 | A1 | * | 1/2005 | Freyman | 424/549 |
| 2005/0234485 | A1 | * | 10/2005 | Seegert et al. | 606/172 |
| 2005/0256588 | A1 | | 11/2005 | Sawa et al. | |
| 2005/0260612 | A1 | | 11/2005 | Padmini et al. | |
| 2006/0073592 | A1 | | 4/2006 | Sun et al. | |
| 2006/0100717 | A1 | | 5/2006 | Abraham et al. | |
| 2006/0210960 | A1 | | 9/2006 | Livesey et al. | |
| 2007/0269791 | A1 | * | 11/2007 | Takami et al. | 435/1.1 |

FOREIGN PATENT DOCUMENTS

| WO | WO 84/04880 | 12/1984 |
|---|---|---|
| WO | WO98/22158 | 5/1998 |
| WO | WO99/08720 | 2/1999 |

OTHER PUBLICATIONS

Pruss et al., Peracetic acid-ethanol treatment of allogeneic avital bone tissue transplants—a reliable sterilization method.Ann Transplant. 2003;8(2):34-42.*
Roberston O H, et al., "The Bactericidal Action of Propylene Glycol Vapor on Microorganisms Suspended in Air. I", Journal of Experimental Medicine (1942) pp. 593-610, Plates 18 and 19, vol. 75.
Lomas R J, et al., "Application of a high-level peracetic acid disinfection protocol to re-process antibiotic disinfected skin allografts", Cell and Tissue Banking (2004) pp. 23-26, vol. 5.
Huang Q, et al., "Banking of non-viable skin allografts using high concentrations of glycerol or propylene glycol", Cell and Tissue Banking (2004) pp. 3-21, vol. 5.
Lakind et al., Critical Reviews in Toxicology 29 (4): 331-365 (1999).
Lomas R J, et al., "Assessment of the biological properties of human split skin allografts disinfected with peracetic acid and preserved in glycerol" Burns, 29 (6): 515-25 (2003).

* cited by examiner

*Primary Examiner*—Maria Leavitt
(74) *Attorney, Agent, or Firm*—Frommer Lawrence & Haug LLP

(57) ABSTRACT

The present invention is a process for preparing soft tissue such as tendons, ligaments, cartilage, fascia, dermis, human valves and human veins for implant in a human and removes cellular components and forms an decellular matrix having as major components collagens and elastins while sterilizing the tissue. The process comprises the following steps:

(1) isolating from a suitable donor a desired soft tissue sample of the biological material;
(2) processing and decellularizing the soft tissue including inspection for visual defects, trimming and soaking the tissue in a detergent depending on whether the tissue is fascia or dermis and rinsing same with sterile water;
(3) sterilizing the soft tissue in a vacuum and soaking the tissue in an antibiotic composition or peracetic acid depending on whether the soft tissue is fascia or dermis and rinsing same;
(4) processing the tissue by cutting the tissue to size and perforating the tissue; and
(5) dipping the tissue in 70% ethanol and packaging the tissue.

14 Claims, 4 Drawing Sheets

SOFT TISSUE PROCESSING

RELATED APPLICATIONS

The present application claims priority from U.S. Provisional Patent Application No. 60/662,078, filed Mar. 16, 2005.

FIELD OF INVENTION

The present invention is generally directed toward methods of treatment of allograft soft tissue including decellularizing and sterilization for implantation into another human being.

BACKGROUND OF THE INVENTION

Techniques for restoring structure and function to damaged tissue are used routinely in the area of reconstructive surgery. Tissue transplantation is another way of restoring function by replacing or rebuilding the damaged tissue. However, problems exist when there is a transfer of biological material from one individual to another. Tissue rejection is a significant risk associated with transplantation, even with a good histocompatability match. Immunosuppressive drugs such as cyclosporin and FK506 are usually given to the patient to prevent rejection. These immunosuppressive drugs however, have a narrow therapeutic window between adequate immunosuppression and toxicity. Prolonged immunosuppression can weaken the immune system, which can lead to a threat of infection.

The present invention is directed toward a process for use in the preparation of acellular, i.e. (essentially lacking in living cells and/or non-living cells,) soft-tissue implants, in commercializable quantities. These implants are derived from tissue products derived from animal or human donors that contain or are devoid of cells. The decellularized grafts produced are significantly improved in long-term durability and function when used in clinical applications.

Various methods have been used in the treatment of soft tissue and such representative methods are disclosed in a number of prior art applications.

The advantages of retaining an acellular matrix, composed primarily of a collagenous component intact, has been explored by Klaus and Duhamel (WO 84/04880) for the production of sterile body implants. In this method, a variety of tissues were extracted sequentially with non-ionic and ionic detergents to yield structures essentially free of cellular membranes, nucleic acids, lipids and cytoplasmic components. The treatment consists of sequential extractions with a non-denaturing detergent and a denaturing detergent to form an acellular matrix of collagen.

U.S. Pat. No. 4,776,853 issued Oct. 11, 1988 is directed toward a process for preparing biological material for implant in a mammal's cardiovascular system, respiratory system or soft tissue. The process comprises: (1) isolating a desired tissue sample of the biological material from a donor; (2) extracting the tissue sample with an hypotonic buffer solution at a mild alkaline pH, the buffer solution including active amounts of proteolytic inhibitors and antibiotics; (3) extracting the tissue sample with a buffered solution having a high concentration of salt, the solution being at a mild alkaline pH and including a non-ionic detergent with protease inhibitors and antibiotics; (4) subjecting tissue sample to enzymatic digestion in a buffered saline solution, the enzymes consisting of purified protease-free dioxyribonuclease and ribonuclease; (5) extracting the tissue sample with an anionic detergent at a mild alkaline pH; and (6) storing the tissue sample in physiologic buffered solutions.

Another soft tissue process is shown in U.S. Pat. No. 6,734,018 issued May 11, 2004 which is directed toward a process for preparing an acellular soft tissue graft for implantation into a mammalian system. The process extracts a soft tissue sample with an extracting solution including one or more nonionic detergents and one or more endonucleases, to produce extracted tissue and treats the extracted tissue with a treating solution including one or more anionic detergents, to produce a treated tissue. The treated tissue is washed with a decontaminating solution including one or more decontaminating agents to produce the acellular soft tissue graft; and acellular soft tissue graft is then stored in a storage solution comprising one or more decontaminating agents.

The soft tissue process of the '018 patent includes the steps of: isolating from a suitable donor a desired tissue sample of the biological material; extracting the tissue with mildly alkaline hypotonic buffered solution of an endonuclease such as Benzonase RTM and a nonionic detergent formulation such as Allowash Solution™ optionally treating the tissue with a hypertonic buffered salt solution; extracting and treating the tissue with a mildly alkaline hypotonic buffered solution of sodium dodecylsulfate, optionally with 0.1 to 0.5 M sodium chloride rendering the solution hypertonic; washing the tissue with ultrapure water followed by a water solution of chlorine dioxide; and storage in a sealed container in isotonic saline, chlorine dioxide or 70% isopropanol.

It can thus be seen that the prior art processes require extensive chemical treatment with a multitude of process steps in an attempt to obtain an acellular soft tissue specimen which has limited shelf life.

SUMMARY OF THE INVENTION

The present invention is a process for preparing soft tissue for implant in a human and removes cellular components forming a decellular matrix having as major components; collagens and elastins while sterilizing the tissue. The process comprises the following steps:

(1) isolating from a suitable donor a desired soft tissue sample of the biological material;

(2) processing and decellularizing the soft tissue including inspection for visual defects, trimming and soaking the tissue in a detergent depending on whether the tissue is fascia or dermis and rinsing same with sterile water;

(3) sterilizing the soft tissue by soaking the tissue in an antibiotic composition and/or peracetic acid depending on the specific tissue and rinsing same to remove residual process chemicals;

(4) processing the tissue by cutting the tissue to size and perforating the tissue; and (5) dipping the tissue in 70% ethanol and 30% water and packaging the tissue.

It is thus an object of the invention to provide decellularized allograft soft tissue for implantation into a human being.

It is another object of the invention to provide decellularized sterilized allograft soft tissue which is packaged for usage as an implant by a surgeon.

It is still another object of the invention to provide decellularized sterilized allograft soft tissue which can be stored for long periods of time for later use by a surgeon for implantation into a human being.

It is yet another object of the invention to provide decellularized sterilized allograft soft tissue which is flexible immediately upon removal from the package.

These and other objects, advantages, and novel features of the present invention will become apparent when considered with the teachings contained in the detailed disclosure along with the accompanying drawings.

DESCRIPTION OF THE INVENTION

Figure 1:
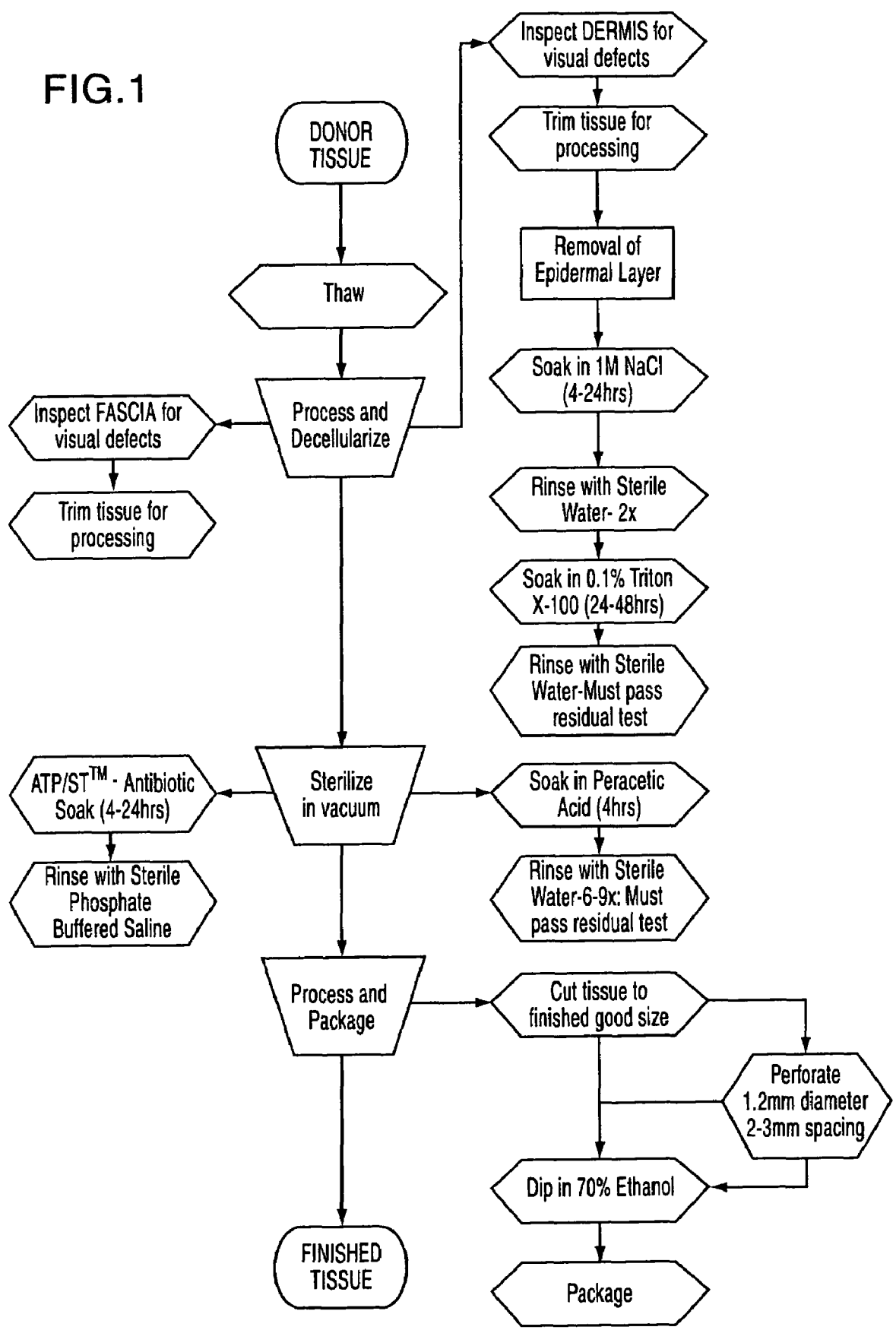
FIG. 1 is a schematic flow chart showing the soft tissue process.
Figure 2:
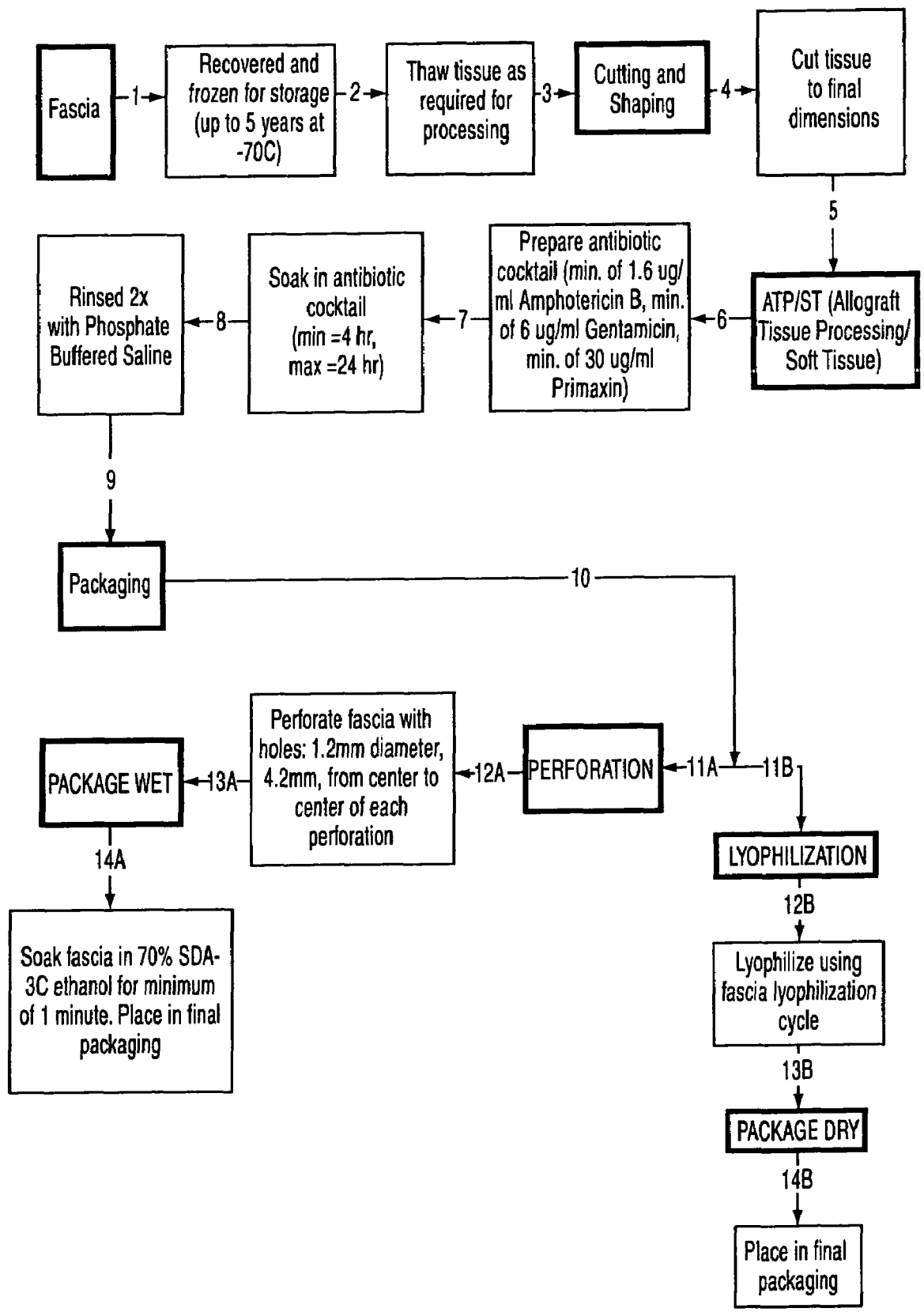
FIG. 2 is a schematic flow chart showing the soft tissue process for fascia.
Figure 3:
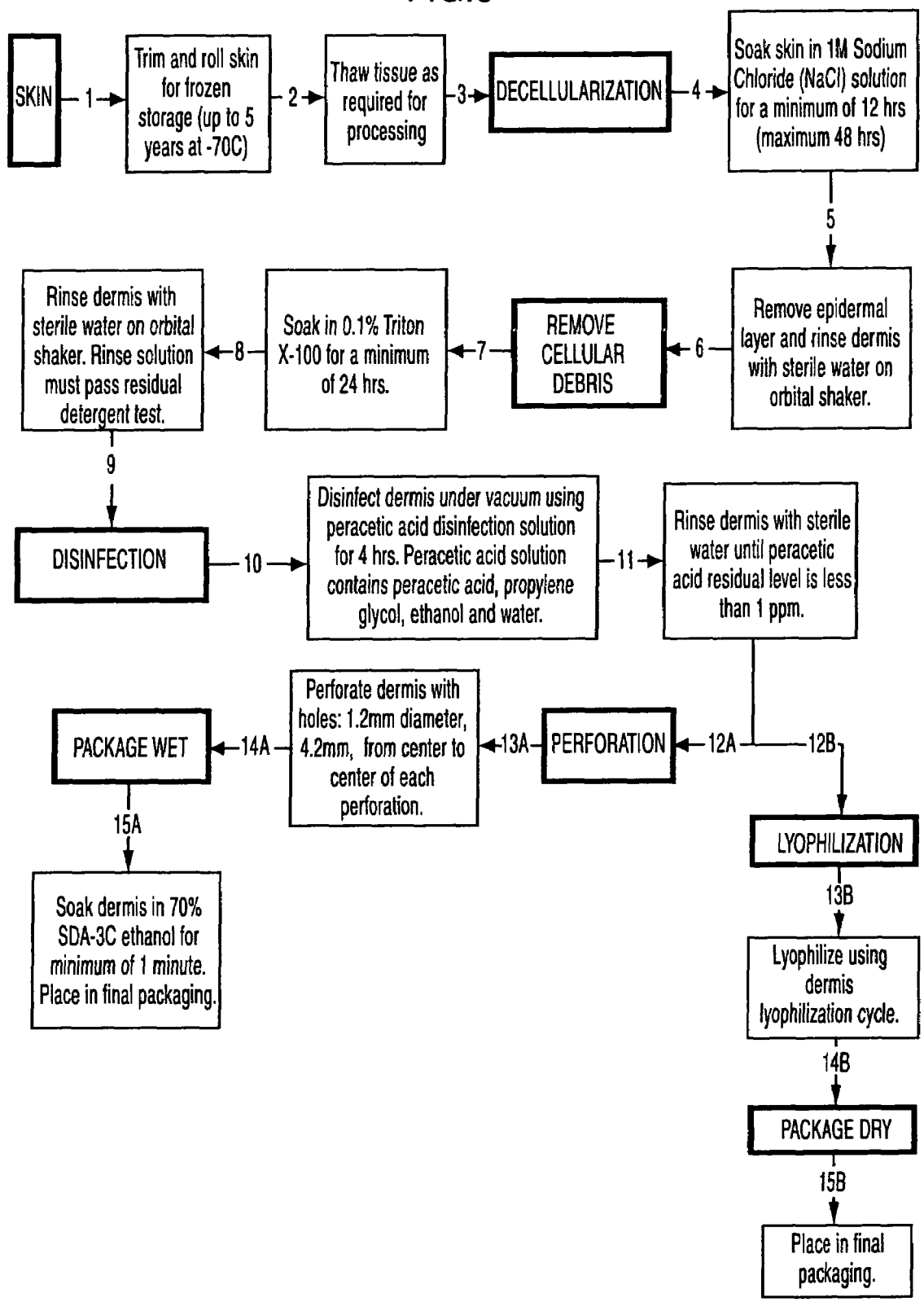
FIG. 3 is a schematic flow chart showing the soft tissue process for dermis.

The present invention is directed towards the preparation of allograft soft tissue such as thawed tissue which is processed and decellularized. The preferred mode and best embodiment of the invention is shown in FIGS. 1-3.

The process uses allograft human soft tissue which has been previously taken from a human donor and frozen for later use. The soft tissue which is envisioned as being used is facia, dermis, cartilage, pericardium, human valves and veins, tendons and ligaments. The soft tissue which has been previously obtained from a donor and frozen is taken from the freezer and thawed. Prior to processing, tissue is inspected for damage (holes or tears) and distinctive features (moles, warts, tattoos) which are removed using a scalpel. Tissue is inspected for hair and the same is removed using forceps. A visual inspection is performed to ensure the tissue has uniform thickness. Any region of non-uniformity or visibly low thickness is removed. Thickness is recorded using a thickness gauge. To identify the orientation (dermal or epidermal side) of tissue such as skin, the skin is positioned such that the epidermis faces the processor and an incision is cut into the upper left corner of each piece of tissue to indicate the epidermal side.

After thawing it is processed and decellularized. For tendons, ligaments, muscle, fascia, muscle, pericardium and dermis soft tissue, the tissue form is inspected for visual defects and then trimmed for procession.

When skin is used the epidermal layer is removed and the tissue is decellularized using a 1M Sodium Chloride (NaCl) solution in a tissue flask and agitated at a speed of 65 RPM on an orbital shaker for a minimum of 12 hours, up to a maximum of 48 hours. The epidermal layer of the skin is removed at this time and rinsed with sterile water. The remaining dermis is replaced in the tissue flasks filled with sterile water and agitated on the orbital shaker for 15 minutes. The sterile water is refreshed and the rinse procedure is repeated one more time for a total of two rinses. Once the rinse is complete, the water is replaced with 0.1% Triton X-100 solution and agitated on the orbital shaker for a minimum of 24 hours, up to a maximum of 48 hours. The dermis is then rinsed with sterile water, replaced in the tissue flasks filled with sterile water, and agitated on the orbital shaker at 65 RPM for 15 minutes. The sterile water is refreshed and the rinse procedure is repeated a minimum of 5 more times. A residual detergent test is performed on the rinsate to ensure the detergent has been adequately removed. The two steps utilizing 1M NaCl and 0.1% Triton soaks may be combined.

The decellularized dermis is subjected to sterilization in a solution containing peracetic acid, alcohol, propylene glycol, and water and soaked and agitated at 65 RPM under vacuum for a minimum of 4 hours, up to a maximum of 8 hours. In certain embodiments, the sterilization solution comprises propylene glycol, ethanol 95% sterile water and peracetic acid 35%. The dermis undergoes a rinse series followed with agitation at 65 RPM under vacuum; two 5-minute rinses, followed by two 10-minute rinses, followed by two 15-minute rinses for a total of 6 rinses. After the last rinse, the residual test is performed on the rinsate to ensure that the peracetic acid has been adequately removed.

Other tissue such as fascia, cartilage, pericardium, tendons and ligaments is soaked in antibiotic soak for 1.5 to 24 hours and rinsed with sterile phosphate buffered saline. If desired the other tissue can also be soaked in 1M NaCl for 1.5 to 48 hours, rinsed with sterile water a plurality of times, then soaked in 0.1% Triton X-100 for 4 to 48 hrs and rinsed with sterile water until a minimal residual amount of detergent is reached. The tissue is soaked in peracetic acid in vacuum for 4 hours and rinsed with sterile water from 6 to 9 times until a minimum residual amount of acid is tested.

The sterilized tissue is cut to finished size. The fascia and dermis can be perforated with holes about 1.2 mm in diameter spaced from each other 2 to 3 mm. The tissue is dipped in 70% ethanol and 30% water and packaged.

EXAMPLE 1

Treatment of Fascia

A desired frozen soft tissue sample is isolated from a suitable donor and then thawed.

The thawed tissue is processed and decellularized and is inspected for visual defects and trimmed.

The trimmed tissue sample is sterilized while soaking the tissue in an antibiotic soak for 1.5 to 24 hours and is rinsed with phosphate buffered saline. If desired at the time of sterilization one or more of the following protease inhibitors may be added; Aminoethylbenzenesulfonyl fluoride HCL (Serine Proteases), Aprotinin (broad spectrum, serine proteases), Protease Inhibitor E-64 (Cysteine Proteases), Leupeptin, Hemisulfate Cysteine Proteases and trypsin-like proteases, Pepstatin A (Aspartic Proteases) and Marmistat (MMP2). If desired a solution with pH of 8.0 can be added which will inhibit lysozomal enzymes The processed soft tissue is placed into a stainless steel container which is filled with an antibiotic solution. The antibiotic solution is a packet of pre-measured antibiotics; Primaxin 0.2168 g/$P_{prim}$, Amphotericin B 0.0297 g/$P_{amph}$, Gentamicin 0.0369 g/$P_{gent}$, respectively, with a tolerance of ±2.5%, and Phosphate Buffered Saline. It should be noted that one of the antibiotics is light sensitive and must be protected from light source. The container or a plurality of containers is placed on a incubator orbital shaker. The purpose of the incubator orbital shaker is to agitate the tissue in the antibiotic solution. The incubator orbital shaker is set at 120 rpm and the temperature reading on the incubator shaker is kept in a range between 35° C. to 39° C. The tissue is soaked and agitated on the incubator shaker for a minimum of 1.5 hours and a maximum of 24 hours in the antibiotic solution.

When rinsing, the tissue is transferred to a 1000 ml polypropylene or Nalgene container. In a graduated beaker 2 packets of phosphate buffered saline are added into 2000 ml of USP purified water and stirred until dissolved. Each polypropylene or Nalgene container containing tissue is filled with the phosphate buffer saline solution and the cap tightened. The tissue is agitated for a minimum of 5 minutes (to a maximum of 20 minutes) and the phosphate buffered saline solution is then emptied out of the container. The rinse steps are repeated; ($2^{nd}$ rinse minimum 5 minute, maximum 20 minutes phosphate buffered saline rinse). A final additional distilled water rinse is then completed. Once the cycle is complete the containers are removed from the orbital shaker. The solution is emptied and the processed tissue is placed on sterile wipes. The soft tissue is now ready to be measured for finishing cutting, perforating and packaging.

Figure 4:
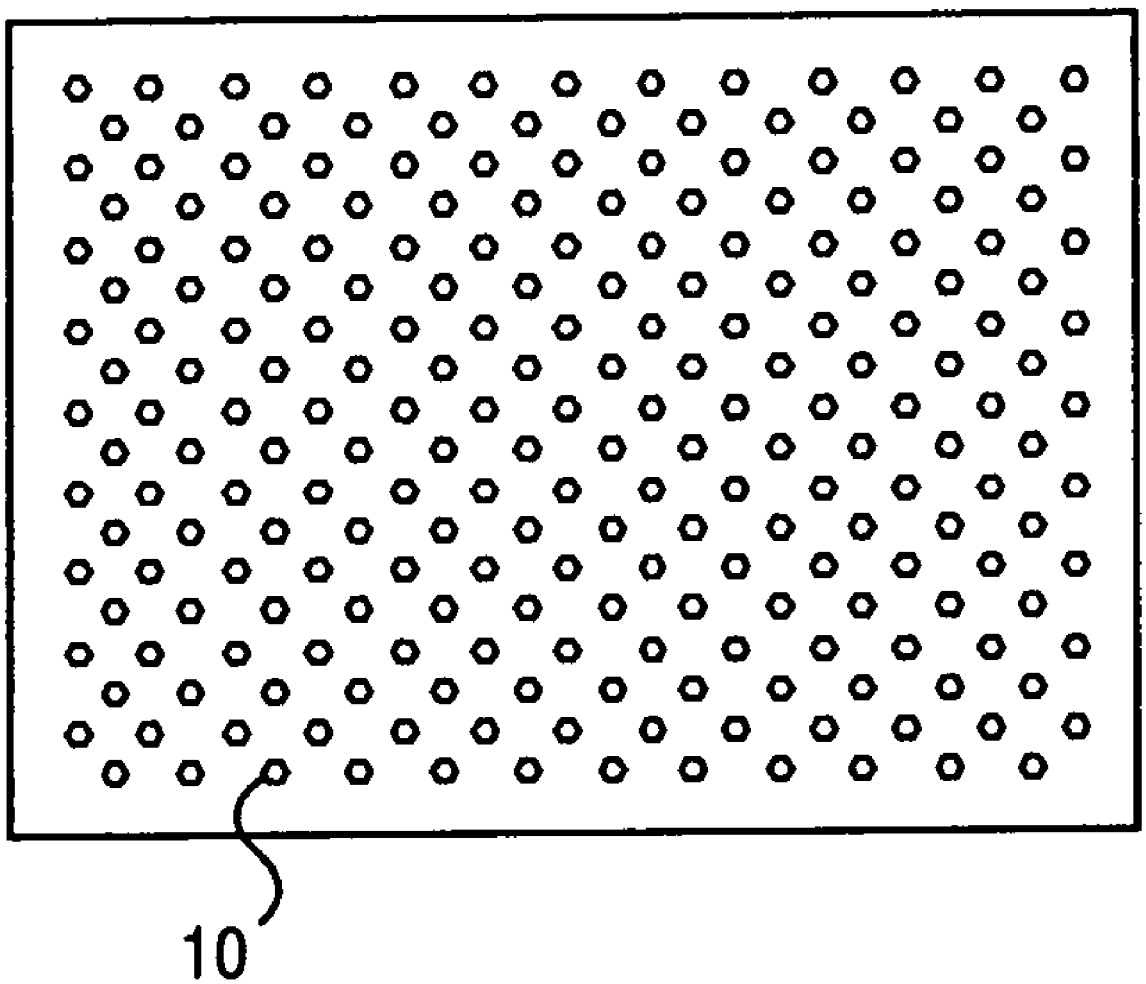
FIG. 4 is a top plan view of a soft tissue strip produced by the process.

The treated fascia tissue is cut to size and may be frozen or lyophilized. If desired, the tissue may be perforated with the perforations 10 spaced 2-3 mm apart and each perforation preferably having a diameter of about 1.2 mm. A view of the finished cut tissue is seen in FIG. 4.

The fascia tissue is immersed in 70% ethanol and 30% water and packaged in a sealed container.

EXAMPLE 2

Treatment of Dermis

Frozen donor tissue is then thawed and then rinsed to maintain moisture. The thawed tissue is processed and decellularized. If desired at the time of decellularization one or more of the following protease inhibitors may be added; Aminoethylbenzenesulfonyl fluoride HCL (serine proteases) (25-100 μm), Aprotinin (broad spectrum, serine proteases) (7.5-30 μm), Protease Inhibitor E-64 (cysteine proteases) (0.05-0.0.20 μm), Leupeptin, Hemisulfate (cysteine proteases) (0.05-0.0.20 μm), EDTA, Disodium (0.025-0.0.10 μm), and trypsin-like proteases, Pepstatin A (Aspartic Proteases). Marmistat (MMP2). The thawed tissue is processed and decellularized and is inspected for visual defects and trimmed.

Once all blood and lipids are removed from the skin, the water is changed with clean sterile water. Impurities are removed from each piece of skin with a scalpel (epidermal side up during this process). Place each skin piece with the epidermal side up on the cutting board or flat surface, check the skin for damage (holes and initial tearing) and for distinctive features (mole, warts, tattoos) and cut these impurities off using a scalpel.

Each piece is checked for hairs and the hairs are removed with forceps after which the skin is rinsed with water. The skin is positioned with the dermis side up (epidermis down) on the cutting board and rectangular skin pieces are cut by removing the rough edges of each piece with one or more uninterrupted cuts using a scalpel and ruler. An incision is cut into the left hand corner of each piece of skin indicating the epidermal side of the skin. A visual inspection is performed to make sure the tissue has a uniform thickness throughout the piece and regions with a visibly low or non-uniform thickness are removed. A thickness measurement is then performed using a thickness gauge. An incision is cut into the upper left corner of each piece of skin so that the epidermal side of the skin is facing the processor to ensure that tissue has a uniform thickness. The skin is decellularized in a sterile tissue culture bottle filled with IL of 1M NaCl. The bottle is sealed in a self-seal pouch and then placed the bottle on its flat side on the shaker with a set speed of 65 rpm's. The bottle(s) is checked after 12 hours to see if the epidermal layers have sloughed off. After the first 12 hour check, the bottle is checked every 2 hours until all epidermal layers have been sloughed. The bottles are removed from the shaker and the NaCl is emptied from the bottle(s). The skin is removed from the bottle and placed on the cutting board with the epidermal side up. The epidermal layers are peeled off with forceps and discarded leaving only the dermal layer (dermis). The bottles are rinsed with sterile water and the peeled skin pieces (dermis) are placed back into the bottle. The bottles are then filled with enough sterile water to submerge the tissue while the bottle is lying flat and the bottle is placed on the shaker which has a preset speed of 65 rpm's. The shaker is set to run for 15 minutes. After running 15 minutes, the bottle(s) are removed and the water is changed with clean sterile water. This rinse is repeated one more time for a total of two times. The bottle(s), are removed from the shaker, emptied and filled with 1 L of 0.1% Triton X-100. The bottle containing the dermis is seated in a self-seal pouch and placed on the shaker set to the speed to 65 rpm's and allowed to shake for 24 to 48 hours. The shaker is stopped after 24 hours or a later time period, the dermis is removed from the bottles and place submerged in a container with sterile water to rinse off the Triton X-100. The tissue is again rinsed with a sterile water for 15 minutes at 65 rpm's for irrigation to rinse off the Triton X-100. The rinse is repeated 5 more times for a total of 6 times. After rinsing a residual detergent test is performed to make sure that the detergent has been removed from the tissue.

The dermis is placed on a screen sterilized in peracetic acid for at least 4 hours in a canister. The dermis can be soaked in peracetic acid for 4 to 8 hours The canister stays on the shaker during the soak with the shaker set at 65 rpm's. The dermis is initially rinsed in sterile water on the shaker at 65 rpm=s for 5 minutes and then rinsed 5 more times; $2^{nd}$ rinse for 5 minutes, $3^{rd}$ and $4^{th}$ rinse for 10 minutes and $5^{th}$ and $6^{th}$ rinse for 15 minutes. After the 6th rinse, a test is performed for the presence of the peracetic acid.

The strips of dermis are taken out of the canister using forceps and placed into a stainless steel basin. The basin is filled with water for irrigation and the residual detergent is rinsed from the surface of the skin. A wipe is placed on the top of a cutting board and moistened with sterile water. The skin is taken from the basin and laid on the cutting board epidermal side down (smooth side up) and measured.

If the dermis is to be lyophilized the skin is placed in a double TYVEK® pouch and the tissue placed in a freezer at −70° C. on the lyophilization staging shelf until the lyophilization is available.

After the $6^{th}$ rinse or upon later removal from the lyophilization, the dermis tissue is cut to size and perforated with the perforations 10 spaced 2-3 mm apart as shown in FIG. 4 with each perforation preferably having a diameter of about 1.2 mm.

The tissue may be lyophilized or is immersed in 70% ethanol and 30% water and packaged for storage in sterile foil.

The dipped tissue is laid flat on screens and placed in double TYVEK® pouches for lyophilization and 1 each TYVEK® pouch is sealed. The package is stored flat in the freezer to prevent the tissue from becoming wrinkled or deformed.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A method for the treatment of human donor dermis to prepare the same for implantation into a human comprising:
   (a) thawing frozen donor dermis and decellularizing the donor dermis;
   (b) inspecting the donor dermis for defects;

(c) trimming the donor dermis for processing;
(d) sterilizing the trimmed donor dermis in a vacuum with a soak in a sterilization solution consisting essentially of propylene glycol, ethanol, water and peracetic acid,
(e) rinsing the material contained in the soak from the donor dermis;
(f) cutting the treated donor dermis to a specific size;
(g) immersing the cut donor dermis in ethanol; and
(h) packaging the ethanol-soaked donor dermis in a sealed package, wherein the donor dermis is flexible upon removal from the package.

2. The method as claimed in claim 1 wherein after (f), the cut dermis is perforated with a plurality of spaced apertures.

3. The method as claimed in claim 1, further comprising adding at least one protease inhibitor during decellularization of the donor soft tissue, wherein the protease inhibitor is selected from the group consisting of: Aminoethylbenzenesulfonyl fluoride HCL (Serine Proteases), Aprotinin (broad spectrum, serine proteases), Protease Inhibitor E-64 (Cysteine Proteases), Leupeptin, Hemisulfate Cysteine Proteases and trypsin-like proteases, Pepstatin A (Aspartic Proteases), and Marmistat (MMP2).

4. The method of claim 1, wherein prior to sterilizing the dermis in (d), decellularizing the dermis comprises:
(i) removing the epidermal layer from skin tissue;
(ii) soaking the remaining skin tissue in 1M NaCl from 1.5 to 48 hours;
(iii) rinsing the NaCl-soaked skin tissue with sterile water a plurality of times to remove the NaCl;
(iv) soaking the treated skin tissue in 0.1% Triton X-100 detergent from 1.5 to 48 hours; and,
(v) rinsing the Triton X-100 detergent-soaked skin tissue with sterile water to remove the detergent to an acceptable level.

5. The method of claim 4, further comprising adding at least one protease inhibitor during decellularization of the dermis, wherein the protease inhibitor is selected from the group consisting of: Aminoethylbenzenesulfonyl fluoride HCL (Serine Proteases), Aprotinin (broad spectrum, serine proteases), Protease Inhibitor E-64 (Cysteine Proteases), Leupeptin, Hemisulfate Cysteine Proteases and trypsin-like proteases, Pepstatin A (Aspartic Proteases), and Marmistat (MMP2).

6. The method of claim 1, wherein the soft donor tissue is soaked in the sterilization solution for about 4 to 8 hours.

7. The method of claim 4, wherein the dermis is soaked in the sterilization solution for about 4 to 8 hours.

8. Dermis tissue prepared according to the method of claim 1.

9. Dermis prepared according to the method of claim 4.

10. The method of claim 1, wherein the sterilization solution in (d) comprises 35% peracetic acid.

11. The method of claim 4, wherein the remaining skin tissue in (ii) is soaked in 1M NaCl from 12-48 hours.

12. The method of claim 4, wherein the treated skin tissue in (iv) is soaked in 0.1% Triton X-100 from 24-48 hours.

13. The donor soft tissue of claim 8, wherein the tissue is less than 1.0 mm thick.

14. The method of claim 1, wherein prior to sterilizing the dermis in (d), decellularizing the dermis comprises:
(i) removing the epidermal layer from skin tissue;
(ii) soaking the remaining skin tissue in 1M NaCl and 0.1% Triton X-100 detergent from 1.5 to 48 hours;
(iii) rinsing the skin tissue from (ii) with sterile water a plurality of times to remove the NaCl and detergent to an acceptable level.

* * * * *

UNITED STATES PATENT AND TRADEMARK OFFICE
CERTIFICATE OF CORRECTION

| | |
|---|---|
| PATENT NO. | : 7,723,108 B2 |
| APPLICATION NO. | : 11/375026 |
| DATED | : May 25, 2010 |
| INVENTOR(S) | : Katherine Gomes Truncale et al. |

It is certified that error appears in the above-identified patent and that said Letters Patent is hereby corrected as shown below:

Col. 7 in Claim 3, Line 16, "soft tissue" should be changed to --dermis--.

Col. 8 in Claim 6, Line 10, "soft donor tissue" should be changed to --donor dermis--.

Col. 8 in Claim 13, Line 23, "soft tissue" should be changed to --dermis--.

Signed and Sealed this

Twenty-ninth Day of June, 2010

David J. Kappos
*Director of the United States Patent and Trademark Office*